(12) United States Patent
Newton et al.

(10) Patent No.: US 9,961,740 B2
(45) Date of Patent: May 1, 2018

(54) METHODS AND APPARATUS FOR CONTROLLING LIGHTING

(71) Applicant: PHILIPS LIGHTING HOLDING B.V., Eindhoven (NL)

(72) Inventors: Philip Steven Newton, Waalre (NL); Bartel Marinus Van De Sluis, Eindhoven (NL); Dzmitry Viktorovich Aliakseyeu, Eindhoven (NL); Tatiana Aleksandrovna Lashina, Eindhoven (NL)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 0 days. days.

(21) Appl. No.: 14/427,741

(22) PCT Filed: Feb. 5, 2014

(86) PCT No.: PCT/IB2014/058806
§ 371 (c)(1),
(2) Date: Mar. 12, 2015

(87) PCT Pub. No.: WO2014/128580
PCT Pub. Date: Aug. 28, 2014

(65) Prior Publication Data
US 2015/0351192 A1    Dec. 3, 2015

Related U.S. Application Data

(60) Provisional application No. 61/766,335, filed on Feb. 19, 2013.

(51) Int. Cl.
*G09F 13/04* (2006.01)
*G09F 13/08* (2006.01)
(Continued)

(52) U.S. Cl.
CPC ....... *H05B 33/0869* (2013.01); *F21V 14/003* (2013.01); *G02B 27/02* (2013.01);
(Continued)

(58) Field of Classification Search
CPC ............ H05B 33/0869; H05B 33/0848; H05B 33/0881; H05B 33/0884; H05B 33/08;
(Continued)

(56) References Cited

U.S. PATENT DOCUMENTS 6,016,038 A    1/2000  Mueller et al.
6,211,626 B1   4/2001  Lys et al.
(Continued)

FOREIGN PATENT DOCUMENTS

JP    2007022721 A    2/2007
JP    2009266625 A    11/2009
(Continued)

*Primary Examiner* — Elmito Breval
*Assistant Examiner* — Jessica M Apenteng
(74) *Attorney, Agent, or Firm* — Meenakshy Chakravorty (57) ABSTRACT

Disclosed are methods and apparatus for lighting control. Presence of an optical element (110, 310, 312, 710A-E, 712, 810) is identified over one or more LEDs (323, 327) and at least one property of the optical element is identified. At least one property of light output of light sources associated with and/or covered by the optical element is adjusted based on the property of the optical element.

19 Claims, 4 Drawing Sheets

(51) Int. Cl.

| | | |
|---|---|---|
| *H05B 33/08* | (2006.01) | |
| *F21V 14/00* | (2018.01) | |
| *G02B 27/02* | (2006.01) | |
| *G06F 3/041* | (2006.01) | |
| *G06F 19/00* | (2018.01) | |
| *G09G 3/34* | (2006.01) | |

(52) U.S. Cl.
CPC .......... *G06F 3/041* (2013.01); *G06F 19/3406* (2013.01); *G09G 3/3406* (2013.01); *H05B 33/0848* (2013.01); *H05B 33/0866* (2013.01); *H05B 33/0872* (2013.01); *G09G 2360/14* (2013.01)

(58) Field of Classification Search
CPC ....... F21V 14/003; G02B 27/02; G06F 3/041; G06F 19/3406; G09G 3/3406; G02F 1/133603; G02F 1/133606; G05D 25/00; H01S 3/10
USPC ...... 362/97.1, 600–634, 235, 311.02, 249.02
See application file for complete search history.

(56) References Cited

U.S. PATENT DOCUMENTS

| | | |
|---|---|---|
| 6,462,868 B1 | 10/2002 | Giesberg et al. |
| 7,543,956 B2 | 6/2009 | Piepgras et al. |
| 2005/0104896 A1 | 5/2005 | Kerr et al. |
| 2006/0145887 A1* | 7/2006 | McMahon ......... H05B 33/0818 340/815.45 |
| 2008/0129453 A1 | 6/2008 | Shanks et al. |
| 2009/0141004 A1* | 6/2009 | Yamazaki ............. G06F 3/0412 345/175 |
| 2009/0167213 A1 | 7/2009 | Hofmann |
| 2010/0213879 A1 | 8/2010 | Chien |
| 2010/0284173 A1 | 11/2010 | Verjans et al. |
| 2011/0115749 A1* | 5/2011 | Yi ......................... G06F 3/0386 345/175 |
| 2012/0230019 A1 | 9/2012 | Peifer |
| 2012/0319586 A1 | 12/2012 | Riesebosch |
| 2013/0286684 A1* | 10/2013 | Holman ................. F21V 17/16 362/612 |
| 2014/0097963 A1 | 4/2014 | Gupta |
| 2015/0185397 A1* | 7/2015 | Klement ............. G02B 6/0035 345/690 |

FOREIGN PATENT DOCUMENTS

| | | |
|---|---|---|
| JP | 2010525567 A | 7/2010 |
| JP | 2011090892 A | 5/2011 |
| JP | 2012164645 A | 8/2012 |
| JP | 2013008695 A | 1/2013 |
| JP | 2013501258 A | 1/2013 |
| WO | 2005024898 A2 | 3/2005 |
| WO | 2009004539 A1 | 1/2009 |
| WO | 2011024109 A1 | 3/2011 |
| WO | 2012056352 A1 | 5/2012 |
| WO | 2012158894 A2 | 11/2012 |

* cited by examiner

METHODS AND APPARATUS FOR CONTROLLING LIGHTING

CROSS-REFERENCE TO PRIOR APPLICATIONS

This application is the U.S. National Phase application under 35 U.S.C. § 371 of International Application No. PCT/182014/058806, filed on Feb. 5, 2014, which claims the benefit of U.S. Provisional Patent Application No. 61/766,335, filed on Feb. 19, 2013. These applications are hereby incorporated by reference herein.

TECHNICAL FIELD

The present invention is directed generally to lighting control. More particularly, various inventive methods and apparatus disclosed herein relate to controlling one or more properties of light output based on one or more identified properties of an attached optical element.

BACKGROUND

Digital lighting technologies, i.e. illumination based on semiconductor light sources, such as light-emitting diodes (LEDs), offer a viable alternative to traditional fluorescent, HID, and incandescent lamps. Functional advantages and benefits of LEDs include high energy conversion and optical efficiency, durability, lower operating costs, and many others. Recent advances in LED technology have provided efficient and robust full-spectrum lighting sources that enable a variety of lighting effects in many applications. Some of the fixtures embodying these sources feature a lighting module, including one or more LEDs capable of producing different colors, e.g. red, green, and blue, as well as a processor for independently controlling the output of the LEDs in order to generate a variety of colors and color-changing lighting effects, for example, as discussed in detail in U.S. Pat. Nos. 6,016,038 and 6,211,626, incorporated herein by reference.

In lighting systems such as those that include LED-based light sources, it is desirable to have control over one or more light sources of the lighting system. For example, it may be desirable to have control of which of a plurality of light sources are illuminated, control of during which time periods one or more light sources are illuminated, and/one or control of one or more lighting parameters of one or more of the light sources. For example, it may be desirable to control which lighting sources are utilized in providing directional light and/or which lighting sources are utilized in providing backlighting.

Direct specification during configuration of the one or more light sources enables selection of lighting parameters. However, such direct specification may suffer from one or more drawbacks such as lack of ability to fine-tune applied lighting, lack of flexibility for adapting to newly introduced environmental objects and/or relocation of existing objects, and/or lack of tailoring of lighting parameters and/or adjustments to specific objects. Remote devices such as smart phones and tablets also enable direct control of one or more light sources. However, such control may suffer from one or more drawbacks such as the need to locate the remote device to control the light source and/or interference with other activities of the remote device. Also, for example, specification via remote devices may be cumbersome and/or may not provide a desired granularity of control. Additional and/or alternative drawbacks of direct specification and/or remote devices may be presented.

Thus, there is a need in the art to provide methods and apparatus that enable control of one or more properties of light output and that optionally overcome one or more drawbacks of existing apparatus and/or methods.

SUMMARY

The present disclosure is directed to lighting control. More particularly, various inventive methods and apparatus disclosed herein relate to controlling one or more properties of light output based on one or more identified properties of an attached optical element. For example, in some embodiments presence of an optical element is identified over one or more light sources and at least one property of the optical element is identified. At least one property of light output of light sources over which the optical element is provided is adjusted based on the property of the optical element.

Generally, in one aspect a method of associating an optical element with at least one light source is provided and includes the steps of: identifying presence of an optical element over one or more covered LEDs of a plurality of LEDs; associating the optical element with one or more of the covered LEDs; identifying at least one property of the optical element; and adjusting at least one lighting property of one or more of the associated covered LEDs based on the property of the optical element.

In some embodiments, the step of identifying the property of the optical element is based on sensing of at least one physical characteristic of the optical element via at least one of the covered LEDs. In some versions of those embodiments the physical characteristic includes at least one of size and shape of the optical element.

In some embodiments, the property of the optical element is indicative of at least one of: whether one or more of the associated covered LEDs provide light output, how many of the associated covered LEDs provide light output, a desired lighting type provided by the associated covered LEDs, a desired light output intensity of the associated covered LEDs, a desired color temperature of the associated covered LEDs, and a desired color of the associated covered LEDs. In some version of those embodiments the desired lighting type may include backlighting and spotlighting.

In some embodiments, the method further includes the step of adjusting at least one lighting property of one or more additional LEDs of the plurality of LEDs, the additional LEDs not being covered by the optical element. In some version of those embodiments the additional LEDs are identified based on proximity of the optical element to the additional LEDs. In some version of those embodiments the additional LEDs immediately surround the optical element. In some version of those embodiments the step of adjusting the at least one lighting property of the additional LEDs is based on association of the covered LEDs with the additional LEDs. In some version of those embodiments the method further includes the step of identifying the additional LEDs based on of the identified at least one property of the optical element. In some version of those embodiments the method further includes the step of identifying the additional LEDs based on the location of at least one additional optical element provided over covered second LEDs of the LEDs, the covered second LEDs being unique from the covered LEDs.

In some embodiments, the step of associating the associated covered LEDs with the optical element is based on at least one physical characteristic of the optical element and may include: initiating a configuration phase; and receiving a configuration confirmation during the configuration phase, the configuration confirmation indicative of associating the associated covered LEDs with the optical element. In some versions of those embodiments the configuration confirmation is received via a remote electronic device.

In some embodiments, the optical element is adhesively attachable over the covered LEDs and/or is a directional optical element and directs light output from the associated covered LEDs in a targeted direction. The optical element may be an active optical element, utilizing at least some of the associated covered LEDs for backlighting. In some versions of those embodiments, light output of at least some of the associated covered LEDs is harvested to power the optical element.

Generally, in another aspect, an active optical element is provided and includes an active display panel, at least one controller coupled to the active display panel and providing content output to the active display panel; and a power source electrically coupled to and powering the active display panel. The active optical element is removably attachable over a surface of a plurality of LEDs. The active optical element has at least one identifiable property, the identifiable property utilized to adjust at least one lighting property of one or more covered LEDs of the LEDs when the active display panel is removably attached over the covered LEDs.

In some embodiments the power source includes at least one light harvesting panel receiving light output from one or more of the covered LEDs when the active display panel is removably attached over the covered LEDS. In some versions of those embodiments the light harvesting panel faces the covered LEDs when the active display panel is removably attached over the covered LEDS.

In some embodiments, the active optical element further includes a frame surrounding the active display panel and covering the power source. In some versions of those embodiments the frame encloses the power source.

Generally, in another aspect, a lighting apparatus including a memory and a controller operable to execute instructions stored in the memory is provided. The instructions stored in the memory include instructions to: identify presence of an optical element over one or more covered LEDs of a plurality of LEDs; associate the optical element with one or more of the covered LEDs; identify at least one property of the optical element; and adjust at least one lighting property of one or more of the associated covered LEDs based on the property of the optical element.

Generally, in another aspect, a lighting system is provided that includes at least one light source generating lighting having at least one adjustable lighting property, at least one sensing LED configured to sense presence of an optical element; and at least one controller in electrical communication with the light source and the sensing LED. The at least one controller: identifies presence of an optical element over one or more covered LEDs of a plurality of LEDs; associates the optical element with one or more of the covered LEDs; identifies at least one property of the optical element; and adjusts at least one lighting property of one or more of the associated covered LEDs based on the property of the optical element.

Other embodiments may include a non-transitory computer readable storage medium storing instructions executable by a processor to perform a method such as one or more of the methods described herein. Yet other embodiments may include a system including memory and one or more processors operable to execute instructions, stored in the memory, to perform a method such as one or more of the methods described herein.

As used herein for purposes of the present disclosure, the term "LED" should be understood to include any electroluminescent diode or other type of carrier injection/junction-based system that is capable of generating radiation in response to an electric signal and/or acting as a photodiode. Thus, the term LED includes, but is not limited to, various semiconductor-based structures that emit light in response to current, light emitting polymers, organic light emitting diodes (OLEDs), electroluminescent strips, and the like. In particular, the term LED refers to light emitting diodes of all types (including semi-conductor and organic light emitting diodes) that may be configured to generate radiation in one or more of the infrared spectrum, ultraviolet spectrum, and various portions of the visible spectrum (generally including radiation wavelengths from approximately 400 nanometers to approximately 700 nanometers). Some examples of LEDs include, but are not limited to, various types of infrared LEDs, ultraviolet LEDs, red LEDs, blue LEDs, green LEDs, yellow LEDs, amber LEDs, orange LEDs, and white LEDs (discussed further below). It also should be appreciated that LEDs may be configured and/or controlled to generate radiation having various bandwidths (e.g., full widths at half maximum, or FWHM) for a given spectrum (e.g., narrow bandwidth, broad bandwidth), and a variety of dominant wavelengths within a given general color categorization.

For example, one implementation of an LED configured to generate essentially white light (e.g., a white LED) may include a number of dies which respectively emit different spectra of electroluminescence that, in combination, mix to form essentially white light. In another implementation, a white light LED may be associated with a phosphor material that converts electroluminescence having a first spectrum to a different second spectrum. In one example of this implementation, electroluminescence having a relatively short wavelength and narrow bandwidth spectrum "pumps" the phosphor material, which in turn radiates longer wavelength radiation having a somewhat broader spectrum.

It should also be understood that the term LED does not limit the physical and/or electrical package type of an LED. For example, as discussed above, an LED may refer to a single light emitting device having multiple dies that are configured to respectively emit different spectra of radiation (e.g., that may or may not be individually controllable). Also, an LED may be associated with a phosphor that is considered as an integral part of the LED (e.g., some types of white LEDs). In general, the term LED may refer to packaged LEDs, non-packaged LEDs, surface mount LEDs, chip-on-board LEDs, T-package mount LEDs, radial package LEDs, power package LEDs, LEDs including some type of encasement and/or optical element (e.g., a diffusing lens), etc.

The term "light source" should be understood to refer to any one or more of a variety of radiation sources, including, but not limited to, LED-based sources (including one or more LEDs as defined above), incandescent sources (e.g., filament lamps, halogen lamps), fluorescent sources, phosphorescent sources, high-intensity discharge sources (e.g., sodium vapor, mercury vapor, and metal halide lamps), lasers, other types of electroluminescent sources, pyro-luminescent sources (e.g., flames), candle-luminescent sources (e.g., gas mantles, carbon arc radiation sources), photo-luminescent sources (e.g., gaseous discharge sources), cathode luminescent sources using electronic satiation, galvano-luminescent sources, crystallo-luminescent sources, kine-luminescent sources, thermo-luminescent sources, triboluminescent sources, sonoluminescent sources, radioluminescent sources, and luminescent polymers.

A given light source may be configured to generate electromagnetic radiation within the visible spectrum, outside the visible spectrum, or a combination of both. Hence, the terms "light" and "radiation" are used interchangeably herein. Additionally, a light source may include as an integral component one or more filters (e.g., color filters), lenses, or other optical components. Also, it should be understood that light sources may be configured for a variety of applications, including, but not limited to, indication, display, and/or illumination. An "illumination source" is a light source that is particularly configured to generate radiation having a sufficient intensity to effectively illuminate an interior or exterior space. In this context, "sufficient intensity" refers to sufficient radiant power in the visible spectrum generated in the space or environment (the unit "lumens" often is employed to represent the total light output from a light source in all directions, in terms of radiant power or "luminous flux") to provide ambient illumination (i.e., light that may be perceived indirectly and that may be, for example, reflected off of one or more of a variety of intervening surfaces before being perceived in whole or in part).

The term "spectrum" should be understood to refer to any one or more frequencies (or wavelengths) of radiation produced by one or more light sources. Accordingly, the term "spectrum" refers to frequencies (or wavelengths) not only in the visible range, but also frequencies (or wavelengths) in the infrared, ultraviolet, and other areas of the overall electromagnetic spectrum. Also, a given spectrum may have a relatively narrow bandwidth (e.g., a FWHM having essentially few frequency or wavelength components) or a relatively wide bandwidth (several frequency or wavelength components having various relative strengths). It should also be appreciated that a given spectrum may be the result of a mixing of two or more other spectra (e.g., mixing radiation respectively emitted from multiple light sources).

For purposes of this disclosure, the term "color" is used interchangeably with the term "spectrum." However, the term "color" generally is used to refer primarily to a property of radiation that is perceivable by an observer (although this usage is not intended to limit the scope of this term). Accordingly, the terms "different colors" implicitly refer to multiple spectra having different wavelength components and/or bandwidths. It also should be appreciated that the term "color" may be used in connection with both white and non-white light.

The term "lighting fixture" is used herein to refer to an implementation or arrangement of one or more lighting units in a particular form factor, assembly, or package. The term "lighting unit" is used herein to refer to an apparatus including one or more light sources of same or different types. A given lighting unit may have any one of a variety of mounting arrangements for the light source(s), enclosure/housing arrangements and shapes, and/or electrical and mechanical connection configurations. Additionally, a given lighting unit optionally may be associated with (e.g., include, be coupled to and/or packaged together with) various other components (e.g., control circuitry) relating to the operation of the light source(s). An "LED-based lighting unit" refers to a lighting unit that includes one or more LED-based light sources as discussed above, alone or in combination with other non LED-based light sources. A "multi-channel" lighting unit refers to an LED-based or non LED-based lighting unit that includes at least two light sources configured to respectively generate different spectrums of radiation, wherein each different source spectrum may be referred to as a "channel" of the multi-channel lighting unit.

The term "controller" is used herein generally to describe various apparatus relating to the operation of one or more light sources. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

The term "addressable" is used herein to refer to a device (e.g., a light source in general, a lighting unit or fixture, a controller or processor associated with one or more light sources or lighting units, other non-lighting related devices, etc.) that is configured to receive information (e.g., data) intended for multiple devices, including itself, and to selectively respond to particular information intended for it. The term "addressable" often is used in connection with a networked environment (or a "network," discussed further below), in which multiple devices are coupled together via some communications medium or media.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, a mouse, keyboard, keypad, various types of game controllers (e.g., joysticks), track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

In lighting systems, such as those that include LED-based light sources, it is desirable to have control over one or more light sources of the lighting system. For example, it may be desirable to have control of a lighting scene, lighting direction, lighting color, illumination intensity, beam width, beam angle, and/or other parameters of one or more of the light sources. Direct specification during configuration of the one or more light sources and/or smart phones and tablets may each enable specification of one or more lighting parameters. However, direct specification may suffer from one or more drawbacks such as lack of ability to fine-tune applied lighting, lack of flexibility, and/or lack of tailoring of lighting parameters. Also, smart phones and/or tablets may suffer from one or more drawbacks such as the need to locate the remote device to control the light source and/or interference with other activities of the remote device.

Thus, Applicants have recognized and appreciated a need in the art to provide methods and apparatus that enable control of one or more properties of light output and that optionally overcome one or more drawbacks of existing apparatus and/or methods.

More generally, Applicants have recognized and appreciated that it would be beneficial to provide various inventive methods and apparatus related to controlling one or more properties of light output based on one or more identified properties of an attached optical element.

In view of the foregoing, various embodiments and implementations of the present invention are directed to lighting control.

In the following detailed description, for purposes of explanation and not limitation, representative embodiments disclosing specific details are set forth in order to provide a thorough understanding of the claimed invention. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatus and methods may be omitted so as to not obscure the description of the representative embodiments. Such methods and apparatus are clearly within the scope of the claimed invention. For example, aspects of the methods and apparatus disclosed herein are described in conjunction with a lighting system having only LED-based light sources. However, one or more aspects of the methods and apparatus described herein may be implemented in other lighting systems that additionally and/or alternatively include other non-LED light sources. Implementation of the one or more aspects described herein in alternatively configured environments is contemplated without deviating from the scope or spirit of the claimed invention. Also, for example aspects of the methods and apparatus disclosed herein are described in conjunction with a single controller and single lighting unit. However, one or more aspects of the methods and apparatus described herein may be implemented in other lighting systems that may include multiple controllers and/or multiple lighting units.

Figure 1:
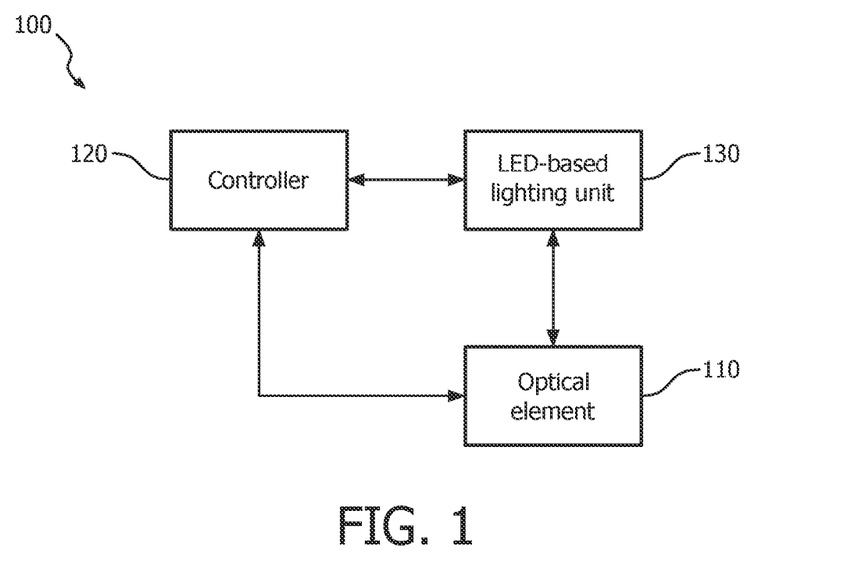
FIG. 1 illustrates a block diagram of an embodiment of a LED-based lighting system having a controller, LEDs, and an optical element.

FIG. 1 illustrates a block diagram of an embodiment of a LED-based lighting system 100. The lighting system 100 includes a controller 120 controlling a plurality of LEDs of at least one LED-based lighting unit 130. The LED-based lighting unit 130 includes one or more LEDs that are configured to generate light output. The control of the LEDs of the LED-based lighting unit 130 is based at least in part on a property of an optical element 110 and/or an attachment location of the optical element 110 on the LED-based lighting unit 130.

In some embodiments, the attachment location and/or the property of the optical element 110 may be communicated to the controller 120 via the LEDs of the LED-based lighting unit 130. For example, as described herein, in some embodiments the LEDs may include one or more LEDs that are operable in a sensing mode and the LEDs may sense presence of and/or a property of the optical element 110 and communicate that presence to the controller 120. In some embodiments presence of and/or the property of the optical element 110 may additionally and/or alternatively be communicated to the controller 120 by the optical element 110 without use of the LEDs. For example, optical element 110 may utilize one or more wireless communications apparatus and methods to communicate directly with the controller 120.

In some embodiments, an initial configuration of the optical element 110 may be achieved via one or more readings from the LEDs of the LED-based lighting unit 130. For example, in some embodiments the LEDs may be utilized in detecting presence of the optical element 110, associating the optical element 110 with control of certain LEDs, and/or identifying a lighting control property of the optical element 110.

The controller 120 controls the LED-based lighting unit 130 based at least in part on identified presence and/or one or more properties of the optical element 110. In some embodiments the LEDs of the LED-based lighting unit 130 are driven by one or more drivers and the controller 120 communicates with the one or more drivers to control the LEDs. In some embodiments the controller 120 may form part of the driver for the LED-based lighting unit 130. In some embodiments the controller 120 communicates with one or more local controllers of the LED-based lighting unit 130 to control the LEDs. For example, a plurality of local controllers may be provided, each controlling one or more LEDs of the LED-based lighting unit 130. In some embodiments the controller 120 itself may include a plurality of local controllers, each controlling one or more LEDs of the LED-based lighting unit 130. The controller 120 may control a single group of LEDs of the LED-based lighting unit 130 or may control multiple groups of LEDs. Embodiments including multiple controllers may optionally incorporate wired and/or wireless communication between the multiple controllers.

In some embodiments, the LED-based lighting unit 130 may include a plurality of LED groupings each including one or more of the LEDs. For example, in some embodiments the LED groupings may each include at least one surface of LEDs and/or one or more portions of a surface of LEDs. A surface of LEDs may include a flat surface, an arcuate surface, a multi-faceted surface, and/or other surface that includes one or more LEDs. Some examples of surfaces of LEDs include a wall, a ceiling, a floor, a column (e.g., a round column, a square column, an elliptical column). One or more aspects of the control of each of the LED groupings may optionally be specific to the individual LED grouping. The LED-based lighting unit 130 may also include one or more sensors that are utilized to detect presence of the optical element 110, associate the optical element 110 with certain LEDs, and/or identify a lighting control property of the optical element 110. In some embodiments the one or more sensors utilized to detect presence of the optical element 110, associate the optical element 110 with certain LEDs, and/or identify a lighting control property of the optical element 110 may include one or more LEDs of the LED-based lighting unit 130 that may be configured to sense light incident thereon. In some embodiments the LEDs configured to sense light may also be configured to generate light output. For example, the LEDs may generate light output in a first mode and be capable of sensing light when they are not in the first mode.

Figure 2:
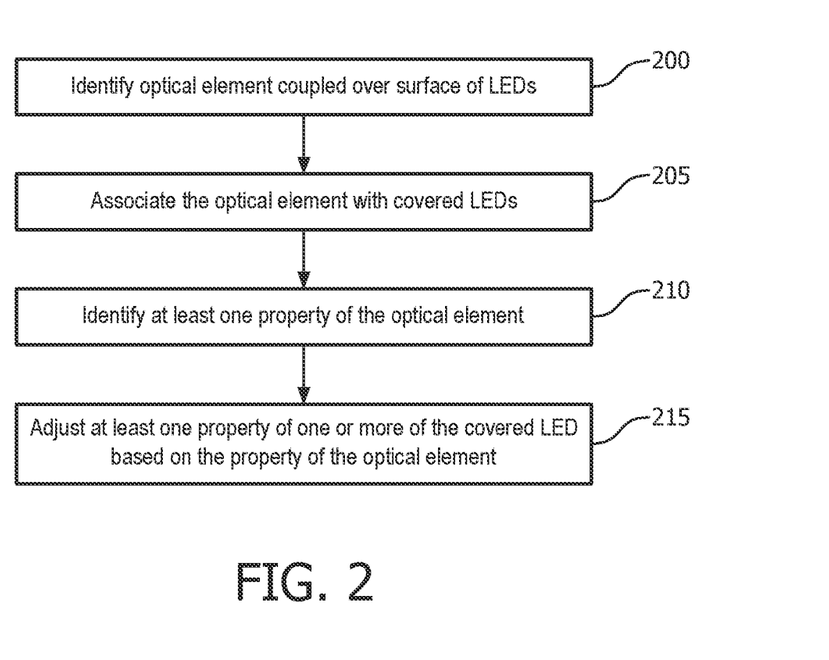
FIG. 2 illustrates a flow chart of an example method of associating an optical element with one or more LEDs.

Referring to FIG. 2, a flow chart of an example method of associating an optical element with one or more LEDs is illustrated. Other implementations may perform the steps in a different order, omit certain steps, and/or perform different and/or additional steps than those illustrated in FIG. 2. For convenience, aspects of FIG. 2 will be described with reference to one or more components of a lighting system that may perform the method. The components may include, for example, one or more of the components of lighting system 100 of FIG. 1 and/or one or more components of FIGS. 3-8B. Accordingly, for convenience, aspects of FIGS. 1 and 3-8B will be described in conjunction with FIG. 2.

At step 200 an optical element coupled over a surface of LEDs is identified. For example, with reference to FIG. 1, the optical element 110 may be coupled over one or more of the LEDs of the LED-based lighting unit 130 and presence of the optical element 110 identified. Also, for example, with reference to FIG. 3, the optical elements 310 and/or 312 may be coupled over the surface of LEDs 320 and presence thereof identified. In some embodiments a user may attach the optical element to any desired location on a surface of LEDs. In some embodiments one or more optical element attachment locations may be indicated. In some embodiments the optical element may include an adhesive that enables adhering of the optical element to the surface of LEDs. For example, the adhesive polyester and/or vinyl may be used and may enable the optical element to be removed with minimal residue left behind and may enable optional re-adhesion to another surface.

In some embodiments, one or more of the LEDs of the surface of LEDs may be utilized to identify the optical element. For example, sensed light values of one or more sensing LEDs may be indicative of whether an optical element is attached to the LED surface over such LEDs. In some embodiments at least one sensed light value of one or more LEDs may be compared to at least one or more baseline light values (e.g., empirical and/or measured in a calibration mode with no optical element present) to determine whether an optical element is attached to the LED surface. For example, in some embodiments at least one sensed light value at one or more LEDs over which the optical element is attached may be compared to one or more sensed light values at those LEDs before the optical element was attached.

For example, a LED may be operated in a sensing mode prior to attachment of the optical element and a first value for the LED determined based on at least one first sensed light value prior to attachment of the optical element. The first sensed light value may sense light incident on the LED in the sensing mode from other light sources directed toward the LED and/or from natural lighting incident on the LED.

The LED may also be operated in a sensing mode after attachment of the optical element and a second value for the LED determined based on at least one second sensed light value after attachment of the optical element. The second sensed light value may be indicative of less light due to the optical element occluding at least some of the light that would otherwise be incident on the LED. The second value may be compared to the first value to determine if an optical element is attached over the LED. For example, if a difference between the first value and the second value satisfies a threshold, then it may be determined that and optical element is attached over the LED.

Figure 3:
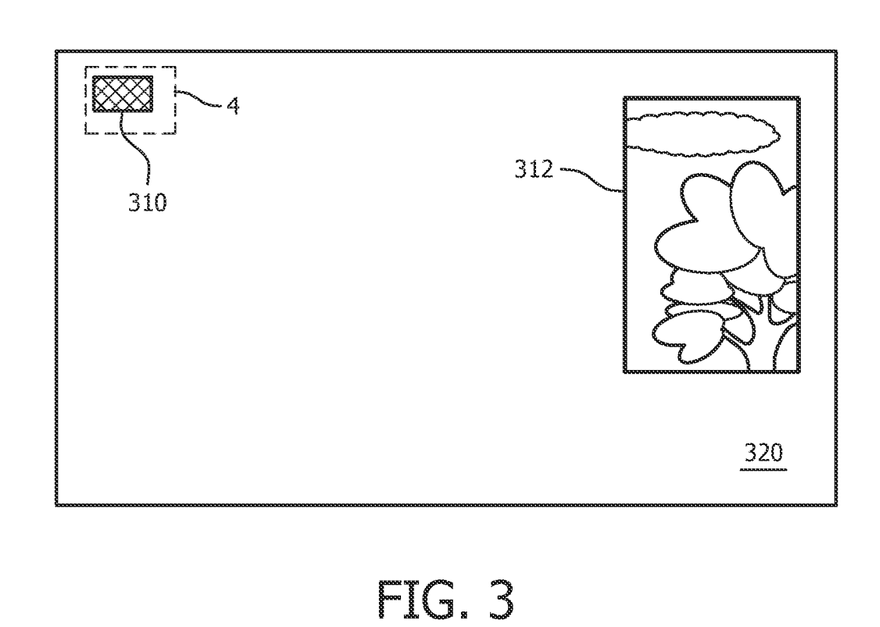
FIG. 3 illustrates an example of a surface of LEDs and optical elements attached to the surface of LEDs.
Figure 4:
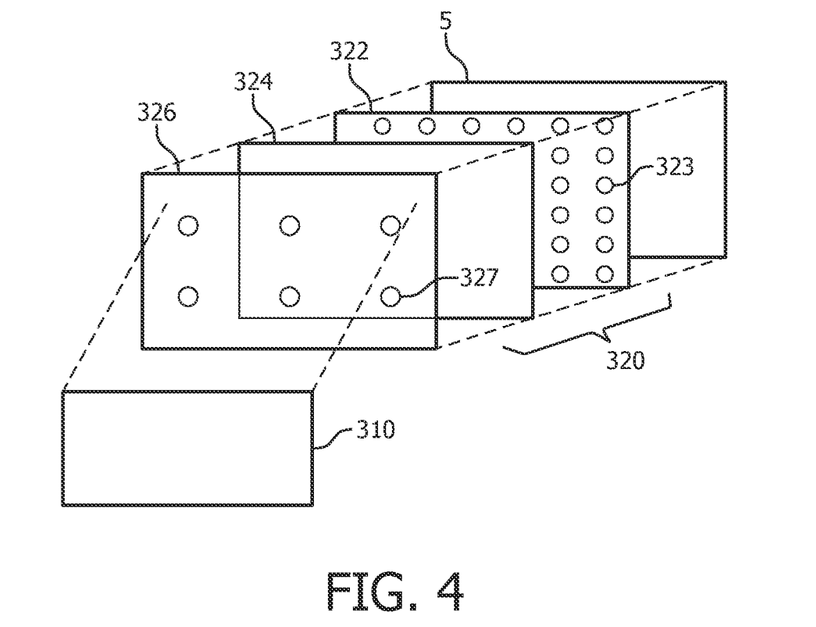
FIG. 4 illustrates an exploded perspective view of a portion of the surface of LEDs of FIG. 4 and one of the optical elements of FIG. 4 exploded away from the example surface of LEDs.

Also, for example, with reference to FIG. 3 and FIG. 4, in some embodiments light generated by one or more LEDs of LED surface 320 may be sensed by one or more other LEDs of the LED surface 320 in identifying presence of an optical element. FIG. 3 illustrates the optical elements 310 and 312 coupled over the surface of LEDs 320. FIG. 4 illustrates an exploded perspective view of the portion of FIG. 3 identified with the reference numeral 4. In FIG. 4 the multiple layers of surface of LEDs 320 are illustrated exploded away from one another and from a wall 5. The optical element 310 is also illustrated exploded away from the portion of the example surface of LEDs 320.

The surface of LEDs 320 includes a first LED layer 322, a diffuse layer 324, and a second LED layer 326. The surface of LEDs 320 may be coupled to the wall 5 or other surface. For example, in some embodiments the first LED layer 322 may be adhesively attached to the wall 5. In some other embodiments the first LED layer 322 may be cohesively formed with the wall 5. The first LED layer 322 includes a plurality of LEDs 323. In some embodiments the spacing and/or power of the LEDs 323 may be such that a substantially homogenous light emitting surface may be created when the diffuse layer 324 is atop the first LED layer 322. In some embodiments the diffuse layer 324 may include a plastic with microstructures that diffuse light output generated by LEDs 323. The diffuse layer 324 may include electrical connections and/or throughways to enable electrical connection of the second LED layer 326. The second LED layer 326 includes a plurality of LEDs 327. As illustrated, in some embodiments the LEDs 327 may be less densely populated than the LEDs 323. In some embodiments individual LEDs of the LEDs represented by 327 may produce a greater lumen output than individual LEDs of the LEDs 323. In some embodiments the LEDS 327 may include optical elements to produce a more directional light output than the LEDs 323.

The LEDs 323 and/or 327 may be utilized as sensing LEDs to identify presence of an optical element. For example, in some embodiments one or more of the LEDs 323 may provide light output and the LEDs 327 may operate in a sensing mode to sense light output received at the LEDs 327. Light output from LEDs 323 that is received at one of the LEDs 327 may indicate an object is present atop the LED 327 and causing some of the light output from the LEDs 323 to be reflected and/or refracted back toward that LED 327. For example, placement of the optical element 312C atop the LEDs 327 may cause at least some of the light output from the LEDs 323 that is incident on the optical element 310 to be reflected back toward the LEDs 327. In some embodiments at least a portion of the optical element 312C that faces the surface of LEDs may be reflective to assist in redirecting light back toward the LEDs 327. In some embodiments a sensed light value at one or more LEDs 327 may be compared to a baseline light value indicative of anticipated light values when no object is present atop or adjacent the respective LEDs 327. In some embodiments the light generated by the LEDs 323 may be coded light to distinguish such light from other light such as ambient light.

In some embodiments, identification of the optical element may be initiated in response to a user indication of an optical element configuration. For example, a user action may trigger the optical element configuration. For example, actuating a button or user interface in communication with controller 120 (e.g., on the device housing the controller 120, on a mobile electronic device (e.g., smart phone, tablet) in communication with the controller 120, other button on the LED-based lighting unit 110) may trigger the optical element configuration.

Also, for example, in some embodiments near field communication (NFC), a radio-frequency identification (RFID) tag, and/or other radio-frequency (RF) device and/or methods may be implemented in an optical element and/or used in combination with installation of an optical element to initiate the optical element configuration. For example, in some embodiments one or more RFID readers may be integrated in the LED-based lighting unit 130 and be in communication with the controller 120. In response to recognizing an RFID tag indicative of an optical element (e.g., embedded in the optical element 110 and/or included with installation material provided with the optical element 110), the controller 120 may cause one or more of the LEDs of the LED-based lighting unit 130 to operate in a sensing mode and identify presence of an optical element attached over such LEDs in response to sensed values.

In some embodiments, the LEDs of a surface of LEDs may intermittently operate in a light sensing mode and monitor for attachment of a new optical element and/or detachment of an existing optical element (e.g., for replacing with a new optical element or repositioning and/or reconfiguration of the existing optical element). For example, in some embodiments one or more specific areas of a surface of LEDs may be designated for attachment of an optical element. One or more LEDs of such areas may be utilized to at least intermittently sense light output and provide sensed values to a controller to recognize attachment and/or removal of an optical element.

In some embodiments, NFC, a RFID tag and/or other RF apparatus and/or method may be implemented in an optical element and/or used in combination with installation of an optical element. The NFC, RFID tag, or other RF signal may be utilized to identify the presence of an optical element over one or more covered LEDs. For example, in some embodiments one or more RFID readers may be integrated in the LED-based lighting unit 130 and be in communication with the controller 120. Recognition of an RFID tag indicative of an optical element may be utilized by the controller 120 to determine that an optical element is provided over one or more LEDs of the LED-based lighting unit 130.

In some embodiments, identification of the optical element may be initiated in response to a user indication of an optical element configuration. For example, a user action may trigger the optical element configuration. For example, actuating a button or other interface element in communication with a controller of the surface of LEDs 320 may trigger the attachable element configuration for attachable elements 310A-E and/or 317.

In some embodiments, near field communication (NFC), a radio-frequency identification (RFID) tag, and/or other radio-frequency (RF) device and/or methods may be implemented in an optical element and/or used in combination with installation of an optical element. Recognition of the RFID tag may initiate the optical element configuration.

At step 205 the optical element is associated with one or more of the covered LEDs over which it is provided. In some embodiments the optical element is associated with all of the covered LEDs over which it is provided. In some embodiments the optical element is associated with the covered LEDs based on the attachment location of the optical element. For example, with reference to FIG. 1, attaching the optical element 110 anywhere over the LEDs of the LED-based lighting unit 130 may associate the optical element 110 with the LEDs of the LED-based lighting unit 130. For example, the optical element 110 may be associated with control of all of the LEDs of the LED-based lighting unit 130. Also, for example the user optical element may be associated with control of a grouping of the LEDs of the LED-based lighting unit 130 that are associated with one or more the LEDs over which the optical element 110 is provided. For example, placing the optical element 110 over at least a first LED may associate the optical element 110 with a first grouping of LEDs that include at least the first LED, whereas placing the optical element 110 over at least a second LED may associate the optical element 110 with a second grouping of LEDs that include at least the second LED. In some embodiments the association with the LEDs over which the optical element is provided may be based on sensing of the optical element by one or more LEDs over which the optical element is located while the LEDs are in a sensing mode.

In some embodiments, the controller 120 may consult a mapping (e.g., stored in memory associated with controller 120) between the LED(s) over which the optical element 110 is attached and other LEDs of the LED-based lighting unit 130 to determine which LEDs to associate with the optical element 110 to enable adjusting at least one light output property of those LEDs in response to the optical element 110. For example, in some embodiments those LEDs over which the optical element 110 is provided may be associated with the optical element 110 and a mapping may be consulted to associated additional LEDs with the optical element 110. For example, a mapping may be consulted to identify those LEDs that surround the optical element 110 and those LEDs surrounding the optical element 110 also associated with the optical element 110. Also, for example, a mapping may be consulted to identify one or more LEDs that are interposed between the optical element 110 and another optical element and those LEDs interposed between the optical element 110 and another optical element also associated with the optical element 110.

In some embodiments, the optical element is associated with the covered LEDs based on placement of the optical element in proximity to the covered LEDs before and/or after attachment of the optical element in its desired installation location. For example, as described herein, in some implementations an optical element configuration may be initiated (e.g., in response to a user action and/or recognition of an RF signal from an optical element). During the optical element configuration the user may place the optical element in proximity to the desired LEDs. Placement of the optical element in proximity to the desired LEDs may provide an indication that the user desires such LEDs to be associated with the optical element.

In some embodiments, the optical element may include NFC, an RFID tag, and/or other RF device that may interface with one or more corresponding RF devices associated with the covered LEDs to provide an indication that the user wishes to control such LEDs. For example, the LED-based lighting unit 130 may include a plurality of RFID readers each corresponding with a grouping of LEDs of the LED-based lighting unit 130 and each in communication with controller 120. After an optical element configuration is initiated, the user may place the optical element 110 in proximity to a desired grouping of LEDs to control, an RFID tag of the optical element 110 may be read by one of the RFID readers, and indication of the RFID tag being read provided to the controller 120. In response, the controller 120 may associate the optical element 110 with the LEDs that are associated with the RFID reader.

In some embodiments, the optical element may be placed over the LEDs to be associated with the optical element during the optical element configuration and one or more of the LEDs to be associated with the optical element may operate in a sensing mode to identify the presence of the optical element. For example, after an optical element configuration is initiated, the user may place the optical element 110 in proximity to a desired grouping of LEDs to associate with the optical element 110, one or more of the LEDs may be operated in a sensing mode and identify presence of the optical element 110, and indication of presence of the optical element 110 provided to the controller 120. In response, the controller 120 may associate that grouping of the LEDs with the optical element 110. The optical element 110 may then optionally be attached over one or more of the associated LEDs.

In some embodiments, an electronic device such as a smartphone and/or tablet may be utilized to associate the optical element with controlled LEDs. For example, as described herein, in some implementations an optical element configuration may be initiated (e.g., in response to a user action and/or recognition of an RF signal). During the optical element configuration the user may utilize the electronic device to associate one or more LEDs with the optical element. For example, after attachment of the optical element 110, the controller 120 may communicate with a mobile electronic device to associate the optical element 110 with a grouping of LEDs. The mobile electronic device may select the grouping of LEDs from predefined groupings and/or create the grouping. In some embodiments LED groupings may be illuminated to provide the user an indication of options for controlled LEDs. For example, in response to attachment of an optical element, LED groupings may be sequentially illuminated and a user may choose one of the LED groupings via an electronic device while a desired of the LED groupings is illuminated.

In some embodiments, the optical element may be associated with one or more LEDs via association with one or more other optical elements and/or one or more LEDs over which other optical elements are provided. For example, in some embodiments a first optical element may be attached over one or more first LEDs and associated with one or more of the first LEDs and a second optical element may be attached over one or more second LEDs and associated with one or more of the second LEDs. The first and/or the second optical elements may be associated with LEDs that are interposed between the first and second optical elements to create an optical effect between the optical elements. For example, with reference to FIG. 7, five separate optical elements 710A-E are attached over a surface of LEDs 720. A series of LEDs 715AE, 715AB, 715AC, and 715AD are generating light output, each extending between optical element 710A and one of the optical elements 710B-E. When providing light output, the series of LEDs 715AE, 715AB, 715AC, and 715AD may visually connect the optical elements 710A-E. In some embodiments the series of LEDs 715AE, 715AB, 715AC, and 715AD are identified and associated with one or more of the optical elements 710A-E based on consultation of a mapping to identify LEDs located between LEDs over which the optical elements 710A-E are provided. In some embodiments LEDs that are covered by one or more of the optical elements 710A-E may optionally provide light output in combination with the series of LEDs 715AE, 715AB, 715AC, and 715AD.

In some embodiments, associating the one or more optical elements with one another may be based on correlation between an identifier of the first optical element and an identifier of the second optical element. Identification of the identifiers for the optical elements may be based on one or more apparatus or methods such as one or more apparatus and/or methods described herein. For example, in some embodiments RFID, NFC, shape, and/or other readings may be utilized to identify the identifier of the optical elements. In some embodiments associating a first optical element with a second optical element may be based on proximity in time within which the two are attached and/or proximity of the locations at which the two are attached. For example, an optical element may be associated with one or more of the locationally closest additional optical elements. Also, for example, an optical element may be associated with one or more of the additional optical elements attached closest in time before and/or after the optical element.

Also, for example, a configuration phase may be utilized whereby when a first optical element is placed on a LED surface and the part of the LED surface associated with the first optical element flashes for a certain time period (e.g., a minute). Within that time period an additional optical element may be associated with the first optical element. This may be done, for example, by attaching an additional optical element. Upon association of the first optical element and the additional optical element, the LEDs associated with the optical elements (e.g., those behind the optical elements and/or those located between the optical elements) may flash a number of times to indicate to the optical elements are now associated with one another.

At step 210, at least one property of the optical element is identified. The property may be based on one or more property identifiable from the optical element. In some embodiments the properties of an optical element may be the same regardless of installation location and/or LEDs associated with the optical element. In some embodiments the properties of an optical element may be based at least in part on one or more installation particulars such as, for example, installation location, LEDs that are associated with the optical element, position and/or properties of other optical element(s). In some embodiments the properties of an optical element may be based on user input. In some embodiments a controller may verify that properties associated with the optical element may be effectuated via the light sources associated with the optical element.

In some embodiments, the property is identified based on LEDs over which the optical element is provided. For example, the shape and/or size of the optical element may be determined based on which of a plurality of LEDs have sensed the presence of the optical element. The shape and/or size may be indicative of a certain property. For example, with reference to FIG. 3, the shape and/or sizes of optical elements 310 and 312 may be determined based on which of the LEDs of LED surface 320 sensed the optical elements 310, 312 thereover and the shape and/or sizes may be indicative of the properties of the optical elements. For example, the shape and size of optical element 310 may indicate that the optical element 310 is an attachable lens element that contains one or more lenses for directing light output in one or more directions. For example, the attachable lens element 310 may include a plurality of directional lenses for directing light output from LEDs over which it is provided toward another surface adjacent LED surface 320. Also, for example, the shape and size of optical element 312 may indicate that it is a free-hanging display element that contains one or more passive and/or active displays that require backlighting from LEDs over which the optical element 312 is provided.

In some embodiments, an opaque surface and/or a reflective surface may be provided on all or portions of the surface of the optical element that faces the surface of LEDs when attached thereto. Such surface may enable and/or increase the ability of the LEDs to sense presence and/or one or more properties of the optical element. For example, in some embodiments a reflective surface may include a plurality of reflective surface sections that may be sensed by LEDs in a surface of LEDs when the reflective surface sections are provided over the surface of LEDs. The number, color, and/or arrangement of the reflective surface sections may be indicative of one or more property of the optical element. For example, in some implementations the reflective surface sections may be arranged according to a predefined arrangement code and that predetermined arrangement code sensed by the LEDs and identified as corresponding to a particular optical element. For instance, reflective sections arranged in a square shape may correspond to a first optical element whereas reflective sections arranged in a triangular shape may correspond to a second optical element. Also, for example, in some implementations the reflective surface sections may additionally and/or alternatively include one or more colors that may be sensed by the LEDs and utilized to determine the particular optical element. For instance, all blue reflective sections may correspond to a first optical element whereas blue and red reflective sections in combination may correspond to a second optical element.

Figure 7:
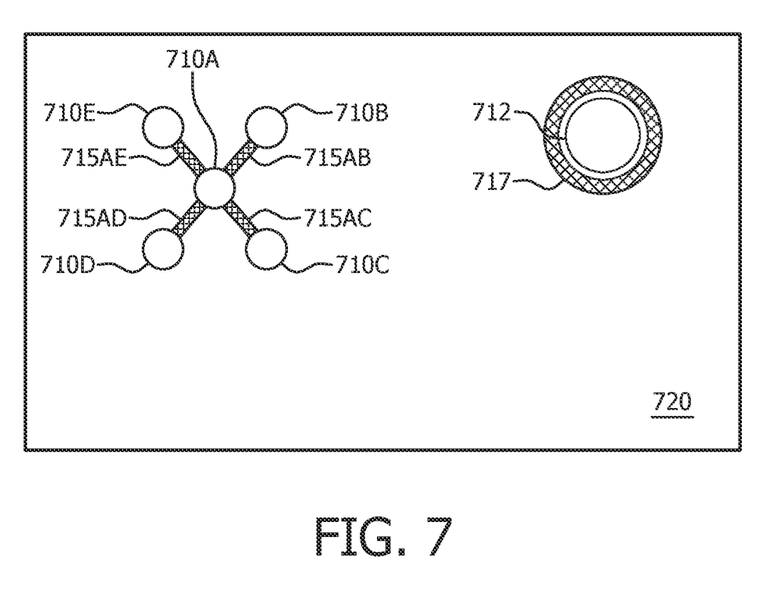
FIG. 7 illustrates another example of a surface of LEDs and optical elements attached to the surface of LEDS.

In some embodiments, the property is identified based on which other optical elements are provided and/or the location of those other optical elements. For example, the shape and size of optical elements 710A-E may indicate that they are each a "spot light" type of optical element that each focuses light output from LEDs over which it is provided in a desired direction. Identification of there being five separate optical elements 710A-E and/or the five separate optical elements 710A-E being attached in a particular arrangement relative to one another may indicate a desired light level and/or color that should be provided by one or more LEDs over which one or more of the optical elements 710A-E are provided. For example, a lower level of desired light output may be associated with each of the optical elements 710A-E when all five are provided as compared to the level of desired light output associated with each of the optical elements when only two of the optical elements 710A-E are provided. Also, for example, when only a single of the optical elements 710A-E is provided it may be indicated that white light output should be provided by the LEDs over which it is provided, whereas when multiple optical elements 710A-E are provided it may be indicated that each should provide a unique color of light output (optionally mixing with one another to form white light output at a desired spot location).

In some embodiments, shape, size, and/or placement of the optical element may be utilized to identify a property of the optical element when the optical element is a passive optical element. A passive optical element is an optical element that does not require power and that optionally does not have any self-contained property transmission capabilities.

In some embodiments, the property is identified based one or more property identifiable via an RF device of the optical element. For example, the optical element may include NFC, an RFID tag, and/or other RF device that may interface with one or more corresponding RF devices associated with the LEDs to provide an indication of one or more properties of the optical element. For example, the RF device may provide a readable code that may be correlated with a corresponding property of an optical element. For example, the LED-based lighting unit 130 may include one or more RFID readers in communication with controller 120. After an optical element configuration is initiated, an RFID tag of the user optical element 110 may be read by one of the RFID readers and indication of one or more properties of the optical element 110 provided to the controller 120 based on the RFID tag. In response, the controller 120 may associate the optical element 110 with the one or more indicated properties.

Also, for example, with reference to FIG. 7, the optical element 712 may include an RFID tag that indicates: LED(s) over which the optical element 712 is provided should be activated to backlight the optical element 712 and that LED(s) around the optical element 712 should be activated to provide an illumination ring 717 around the optical element 712. The required light source settings may be based on information obtained via the optical element and/or may be based on light source capabilities of the corresponding controlled light sources.

In some embodiments, an electronic device such as a smartphone and/or tablet may be utilized to provide an indication of one or more properties of the optical element. For example, as described herein, in some implementations an optical element configuration may be initiated (e.g., in response to a user action and/or recognition of an RF signal). During the optical element configuration the user may utilize the electronic device to identify one or more properties of the optical element (e.g., by selecting the optical element on the electronic device, scanning a QR code associated with the optical element via the electronic device).

For example, with reference to FIG. 7, a controller may communicate with a mobile electronic device to identify properties of the optical elements 710A-E. The mobile electronic device may select the properties from predefined properties and/or specify the properties. For example, in some embodiments the optical elements 710A-E may be identified utilizing the mobile electronic device (e.g., via a camera of the mobile electronic device and/or NFC of the mobile electronic device) and a plurality of predefined properties presented to the user. The properties may be based on the identification of the optical elements 710A-E and/or the capabilities of the LEDs controlled in response to the optical elements 710A-E.

For example, a first predefined property for the optical elements 710A-E may indicate that LEDs over which each of the optical elements 710A-E are located should provide low intensity backlighting light output and that each of the series of LEDs 715AE, 715AB, 715AC, and 715AD should generate low intensity diffuse light output. Also, for example, a second predefined lighting control property for the optical element 710 may indicate that LEDS over which each of the optical elements 710A-E should provide high intensity spotlighting light output and that only selected of the series of LEDs 715AE, 715AB, 715AC, and 715AD should generate light output. Additional and/or alternative properties may be defined. For example, in some properties none of the series of LEDs 715AE, 715AB, 715AC, and 715AD should generate light output.

At step 215 at least one property of one or more of the covered LEDs is adjusted based on the property of the optical element that was identified at step 210. For example, in response to identification of size and/or location of the optical element, one or more LEDs behind the optical element may be configured to generate light output. The LEDs may be configured to generate light output whenever the optical element is attached and/or may be controlled (e.g., on/off, intensity, color) via one or more interface elements such as, for example, one or more switches that control the LEDs, a mobile device that controls the LEDs, based on a schedule, and/or based on input from one or more sensors.

Also, for example, in response to identification of a property of an optical element that identifies a particular color temperature that is desired from covered LEDs, the color temperature of the LEDs covered by the optical element may be adjusted to substantially conform with the desired color temperature. Also, for example, in response to identification of a property of an optical element that identifies a particular lumen output that is desired from covered LEDs, the brightness of one or more of the LEDs covered by the optical element may be adjusted and/or the number of LEDs that are covered by the optical element which are illuminated to substantially conform with the desired color temperature. One or more controllers and/or drivers in communication with the covered LEDs may effectuate the adjustment to the LEDs based on attachment of the optical element over the LEDs.

Also, for example, in response to identification of a property of optical element 310 that identifies optical element 310 as an attachable lens element that contains one or more lenses for directing high intensity light output in one or more directions, then one or more LEDs 327 of second layer of LEDs 326 that are covered by optical element 310 may provide light output. The higher powered light output of LEDs 327 may provide light output that is better suited for providing high intensity directed light via optical element 310. Optionally, one or more LEDs 323 of first layer of LEDs 322 that are covered by optical element 310 may not provide light output. Also, for example, in response to identification of a property of optical element 312 that identifies optical element 312 as a free hanging display that desires substantially uniform backlighting, then one or more LEDs 323 of first layer of LEDs 322 that are covered by optical element 312 may provide light output. The lower powered light output of LEDs 322 and diffuse layer 324 may provide light output that is better suited for providing back lighting for optical element 312. Optionally, one or more LEDs 327 of second layer of LEDs 326 that are covered by optical element 312 may not provide light output.

In some embodiments, one or more LEDs that are not covered by the optical element may additionally and/or alternatively be adjusted based on the property of the optical element. For example, with reference to FIG. 7, LEDs 715AE may provide light output in response to identification of the location of optical elements 710A and 710E. Also, for example, illumination ring 717 may provide light output in response to identification of the location of optical element 712. One or more LEDs that are covered by optical element 712 may also optionally provide light output.

Figure 5:
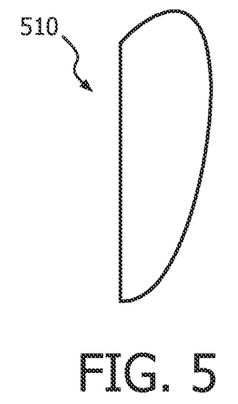
FIG. 5 illustrates a side view of an example optical element.

FIG. 5 illustrates a side view of an example optical element 510. The optical element 510 has a flat surface which may be attached over a surface of LEDs. The optical element 510 also has an asymmetric shape to direct light that enters the optical element 510 from the LEDs over which it is provided in an asymmetric direction out of the optical element 510.

Additional and/or alternative optical elements may be provided. For example, in some embodiments translucent decoration stickers which evoke a particular light effect may be provided. Also, for example, in some embodiments an optical element may additionally and/or alternatively include one or more structures such as grooves and/or slits to direct the light from one or more LEDs over which it is provided in a desired direction. Also, for example, in some embodiments an optical element may additionally and/or alternatively include a barrier and/or a lenticular lens array to direct the light from one or more LEDs over which it is provided in various directions. Also, for example, in some embodiments an optical element may additionally and/or alternatively be shaped to create a main bright spot from light output of one or more LEDs over which it is provided and may also include spherical aberrations which will result in one or more secondary bright rings from one or more LEDs over which it is provided. The secondary bright rings may be provided around the main bright spot. Also, for example, in some embodiments an optical element may additionally and/or alternatively include a diffraction grate.

Figure 6A:
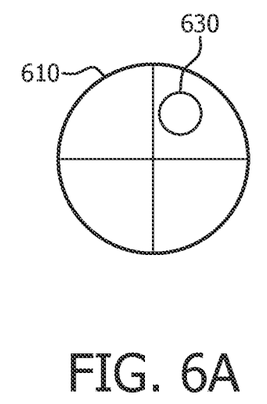
FIGS. 6A and 6B illustrate an alignment portion of an example optical element provided over an LED producing light output.
Figure 6B:
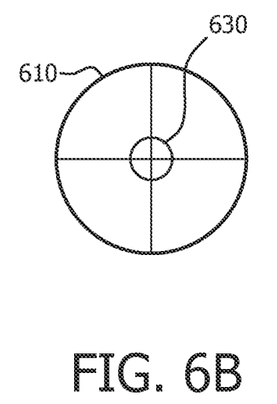
Figure 8A:
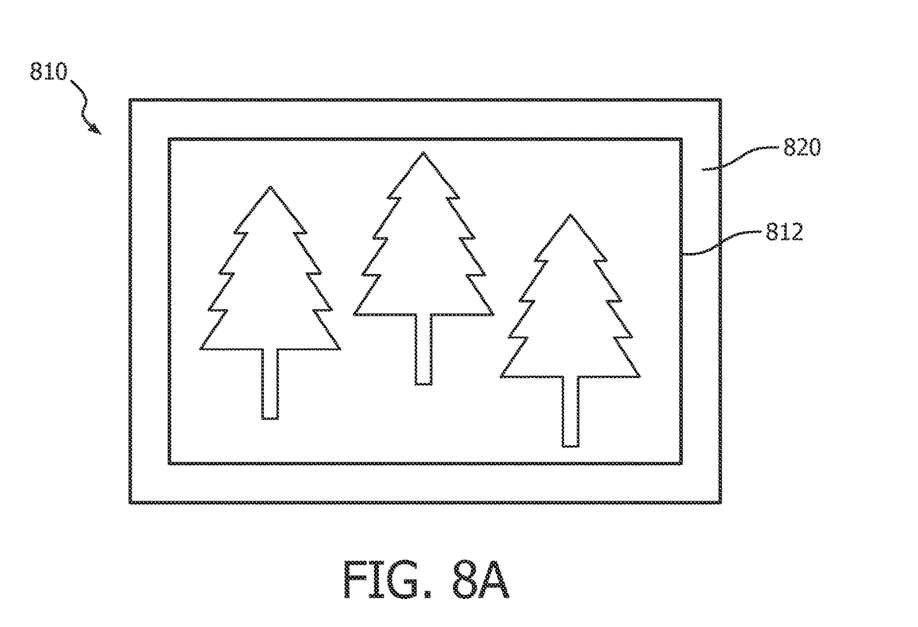
FIG. 8A illustrates an example of an active optical element.

FIGS. 6A and 6B illustrate an alignment portion 610 of an example optical element provided over an LED 630 producing light output. In some embodiments, the alignment portion 610 may be generated by an active display panel of the optical element. For example, the active display panel 812 of active optical element 810 may generate the alignment portion 610 during alignment of the active optical element 810 over a surface of LEDs. In some embodiments the alignment portion 610, or other alignment display may be generated during a configuration phase in which the optical element is coupled over a surface of LEDs and/or associated with one or more covered LEDs. In some embodiments the alignment portion 610, or other alignment portion may be provided on a detachable sticker provided on the optical element that may be removed after placing the optical element at the desired location on the LED surface. For example, a transparent sticker having the alignment portion 610 may be removably attached to optical element 312 during positioning thereof on the surface of LEDs 320.

Alignment portion 610 includes a circle with a cross hair. A LED 630 on the LED surface produces a visible light dot, enabling the user to optimally align the alignment portion 610 with the light dot. For example, the user may move the optical element so that the alignment portion moves from a position as shown in FIG. 6A to a position as shown in FIG. 6B, which reflects the optimal alignment of the optical element 610. The LED 630 may be indicated as the alignment LED. For example, the LED 630 may be the only LED of the LED surface that is illuminated during positioning of the optical element. Also, for example, the LED 630 may blink during positioning of the optical element to indicate it is the alignment LED. Also, for example, the LED 630 may be generate light output at a higher or lower intensity than other LEDs of the surface of the LEDs during positioning of the optical element. Additional LEDs may optionally be utilized in addition to LED 630 during positioning of the optical element. For example, multiple alignment portions 610 may be provided, with each being alignable with one or more LEDs. In some embodiments which LED is the alignment LED may be based on one or more properties of the optical element identified at step 210. For example, the particular alignment LED may be based on an identified shape, size, and/or other property of the optical element.

Figure 8B:
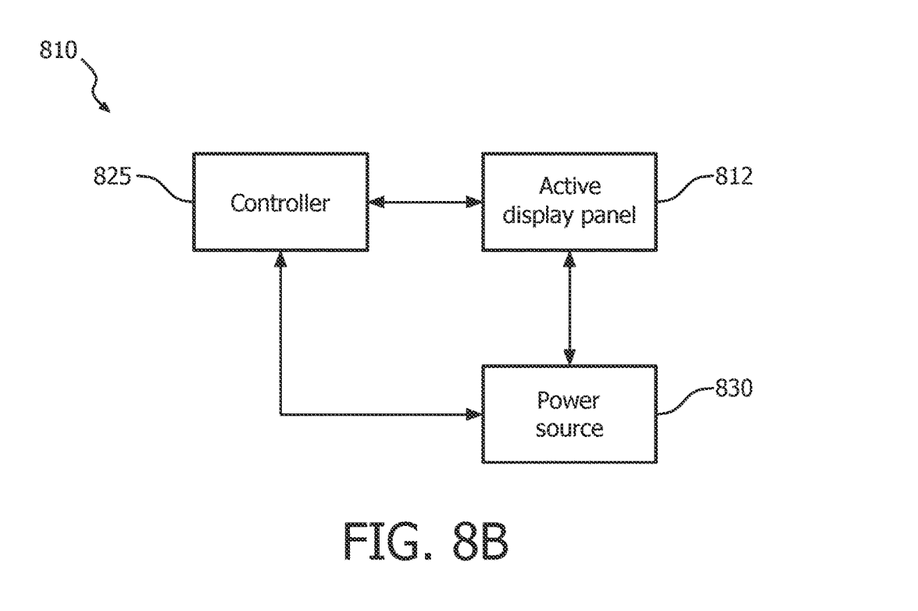
FIG. 8B illustrates a block diagram of the active optical element of FIG. 8A.

FIG. 8A illustrates an example of an active optical element 810 having an active display panel 812. FIG. 8B illustrates a block diagram of the active optical element 810 of FIG. 8A. In some embodiments the active display panel 812 may be an LCD display. In some embodiments the active display panel 812 may be an OLED display. In some embodiments the active display panel 812 may be a bi-stable liquid crystal display. In some embodiments the active display panel 812 may be utilized to provide active audio and/or video to a user. For example, the active display panel 812 may be utilized as a television screen. Also, for example, the active display panel optical element 812 may be utilized as a virtual window and/or skylight.

The active optical element 810 includes at least one controller 825 coupled to the active display panel 812. The controller 825 may provide content output for display on the active display panel 812. In the illustration of FIG. 8A, the content includes three trees that are being displayed on the active display panel 812. In some embodiments the content output may be based on content stored in memory associated with the controller 825. In some embodiments the content output may be based on content received via a wireless signal such as a Wi-Fi signal and/or coded light output from a surface of LEDs over which the display panel optical element 812 is attached and/or from other LEDs. For example, LEDs embedded in the surface of LEDs that are not covered by a diffuser but instead are normally used to create accent or spot lighting (such as LEDs 327 of FIG. 4) may be utilized to transmit data to one or more sensors in communication with the controller 825. For example, active optical element 810 may be attached to LED surface 820 and sensors provided on a rear surface of a frame 820 provided around the active display panel 812. LEDs 327 over which the frame 820 is provided may transmit encoded light to the sensors on the rear surface of the frame 820. Backlighting may be provided to the active display panel 812 via LEDs 322 over which the active display panel 812 is provided.

In some embodiments, the content output may be based on content received via a Zigbee communications protocol. In some embodiments the content may include active content that is refreshed (e.g., refreshed at 240 Hz, refreshed at 60 Hz, and/or refreshed at other frequency). The refresh rate of content may be dependent on the content being displayed. For example, it may be desirable to have a higher refresh rate when the active display panel optical element 812 is utilized to view a movie than when it is utilized as a virtual window with a relatively slow changing outdoor scene being displayed.

A power source 830 is coupled to and powers the controller 820 and the active display panel 812. In some embodiments the power source 830 may include one or more batteries. In some embodiments the batteries may be behind and/or encased within the frame 820 provided around the active display panel 812. In some embodiments the power source 830 may include one or more light harvesting panels that harvest available light to provide power for the active display panel 812, controller 825, and/or other electronics of active optical element 810 (e.g., any provided communications electronics). For example, in some embodiments the light harvesting panel may face one or more LEDs over which the active optical element 810 is provided and the LEDs may be powered at least intermittently to provide power to the active optical element 810 via the light harvesting panel. For example, the active optical element 810 may include a light harvesting panel on a rear surface of frame 820 that harvests light from one or more LEDs that are generating light output behind the frame 820 when the active optical element 810 is attached to a surface of LEDs. In some embodiments any light harvesting panel may optionally be provided in combination with a battery and optionally provide a charge for the battery. For example, the light harvesting panel may charge the battery when the active display panel 812 and/or other electronics of the active optical element 810 are not in use. Also, for example, the light harvesting panel may additionally and/or alternatively be utilized to supplement any battery and directly provide power to one or more aspects of the of the active optical element 810 when those aspects are in use.

In some embodiments the configuration of the power source 830 may be based on one or more characteristics of the active optical element 810. For example, in some embodiments the configuration of the power source 830 may be based on power consumption of the active display panel 812. As an example, in embodiments where the active display panel 812 is an LCD panel the configuration of the power source 830 may be based on the amount of power the LCD panel consumes. Also, for example, in some embodiments the configuration of the power source 830 may be based on power consumption of other components associated with the active optical element 810 such as the controller 825 and/or a communications transmitter/receiver.

In some embodiments the power source 830 may include multiple lithium polymer battery cells to power the active display panel 812 and/or associated electronics. Combining multiple lithium polymer battery cells may deliver higher voltages and/or more capacity. In some embodiments the amount of battery cells needed may be based on the desired amount of time which the display panel optical element 812 may be powered. For example, to calculate the amount of battery cells needed, the power density of a single battery cell may be determined and compared to the desired running time of the active display panel 812 and associated electronics and the power consumption of the active display panel 812 and associated electronics.

In some embodiments the frame 820 may be sized so that any power source 830 and/or any other components associated with the active display panel optical element 812 may be covered by the frame 820. For example, in some embodiments the electronics and batteries may be enclosed in and/or covered by the frame 820. Also, for example, in some embodiments any light harvesting panel may be provided on a backside of the frame 820 and covered by the frame 820.

In some embodiments, the number of LEDs on the LED surface that need to generate light output and/or the light output intensity of such LEDs needed to provide backlight for the active display panel 812 may be based on one or more properties of the active display panel 812. In some embodiments such one or more properties may be identified by a controller associated with the surface of LEDs such as described with respect to step 210. For example, in some embodiments the number of LEDs on the LED surface that need to generate light output and/or the light output intensity of such LEDs may be based on a transmission efficiency of the active display panel 812. Also, for example, in some embodiments the number of LEDs on the LED surface that need to generate light output and/or the light output intensity of such LEDs may be based on one or more desired values identified based on one or more property of the active optical element 810.

In some embodiments, presence of the active optical element 810 over a surface of LEDs may be detected as described herein with respect to step 200. For example, the active optical element 810 may be detected by one or more sensing LEDs of the LED surface based on reflection of light output from one or more light output LEDs of the LED surface off of the active optical element 810 and back to the sensing LEDs. In some embodiments the presence of the active optical element 810 over a surface of LEDs may be detected in response to a user indicated configuration phase as described herein. For example, the user may indicate that he wishes to initially place the active optical element 810 and/or move the active optical element 810 to a new location. This may put the system into the commissioning phase whereby LEDs in the LED surface emit a low level pulsating light signal. The frequency of the pulsating light signal may be chosen such that it is not perceived by the user. By using a second LED layer as sensors (e.g., as described with respect to FIG. 4) when in the commissioning phase, the pulsating light reflected off the active optical element 810 can be detected. This reflected signal will be much larger in places where there is an object attached to the LED surface. The strength of this reflected signal may be used to determine the placement of an object attached to the LED surface. Once all the static objects are detected, the system may indicate this by a low frequency pulsating signal that can be perceived by the user (e.g., one or more LEDs blink several times). Once the user sees this he can place the active optical element 810 at the desired location on the LED surface. Once this is done the user may indicate this to the system, which may then again use the second LED layer as sensors and compare the earlier detected objects with the new detected objects to determine the location of the active optical element 810 on the LED surface. Additional and/or alternative steps may be utilized to identify presence of the active optical element 810 and/or one or more properties of the active optical element 810 such as size. For example, one or more of the steps described herein with respect to the method of FIG. 2 may optionally be utilized.

In some embodiments, an affixation method and/or apparatus for the active optical element 810 may be chosen that does not require structural (semi-permanent) fixation methods (e.g., drilling holes). In some embodiments the affixation method and/or apparatus may be based on the weight of the active optical element 810 and/or the size of an affixation surface such as all or portions of the back surface of frame 820. For example, in some embodiments the active display element 812 may be an LCD sheet that is approximately 52" diagonally and the frame 820 may be approximately 2 cm from the edge of the display element 812 to the edge of the frame 820. A required adhesive strength may be determined based on the surface area of the frame 820 and the weight of the active optical element 810. For example, it may be determined that an adhesive material with an adhesive strength of at least 14 kg/m2 or roughly 140 N/m2 may be needed for a 52" active display element 812 with a 2 cm frame 820, wherein the adhesive material is attached to all or portions of the rear surface of the frame 810. Other adhesive materials and/or other affixation materials may be utilized. The strength of the adhesive material may be less and/or greater dependent on, for example, the weight of the active optical element 810 and/or desired adhesion integrity.

In some embodiments an optical element that utilizes power (e.g., for an active display panel and/or one or more active communications electronics), the optical element may be at least in part powered inductively. For example, small coils may be embedded in the LED surface over which the optical element is attached and may be utilized to inductively power the optical element. Also, for example, in some embodiments the optical element may be powered capacitively. For example, an electromagnetic field may be utilized to power the optical element. Additional and/or alternative apparatus and methods may be utilized to power an optical element, when the optical element requires power. In some embodiments those apparatus and/or methods may enable powering of the optical element independently of requiring a connection to the mains power supply.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

Also, reference numerals appearing between parentheses in the claims, if any, are provided merely for convenience and should not be construed as limiting the claims in any way.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of associating an optical element with at least one light source, comprising:
    identifying presence of the optical element covering one or more portions of a surface of a plurality of light-emitting diodes, wherein said presence is based on sensing by one or more light-emitting diodes that are configured to sense the presence of the optical element covering one or more portions of the surface, said optical element being removably attachable over the surface of said plurality of light-emitting diodes;
    communicating said presence of the optical element covering one or more portions of the surface to a controller;
    associating the optical element with at least one covered light-emitting diode;

identifying at least one identifiable property of the optical element based on sensing of at least one physical characteristic of the optical element via at least one of the covered light-emitting diodes; and adjusting at least one lighting property of the at least one associated covered light-emitting diode based on the identifiable property of the optical element.

2. The method of claim 1, wherein the physical characteristic includes at least one of size and shape of the optical element.

3. The method of claim 1, wherein the identifiable property of the optical element is indicative of at least one of: whether the associated covered light-emitting diode provides light output, whether there are additional associated covered light-emitting diodes providing light output, a desired lighting type provided by the at least one associated covered light-emitting diode, a desired light output intensity of the at least one associated covered light-emitting diode, a desired color temperature of the at least one associated covered light-emitting diode, and a desired color of the at least one associated covered light-emitting diode.

4. The method of claim 1, further comprising adjusting at least one lighting property of one or more additional light-emitting diodes of the plurality of light-emitting diodes, said additional light-emitting diodes not being covered by the optical element.

5. The method of claim 4, wherein the additional light-emitting diodes are identified based on proximity of the optical element to the additional light-emitting diodes.

6. The method of claim 4, further comprising identifying the additional light-emitting diodes based on the identified at least one lighting property of the optical element.

7. The method of claim 4, further comprising identifying the additional light-emitting diodes based on the location of at least one additional optical element provided over covered second light-emitting diodes of the light-emitting diodes, the covered second light-emitting diodes being unique from the at least one covered light-emitting diode.

8. The method of claim 1, wherein the step of associating the at least one associated covered light-emitting diode with the optical element is based on at least one physical characteristic of the optical element.

9. The method of claim 1, wherein the step of associating the at least one associated covered light-emitting diode with the optical element includes:
    initiating a configuration phase; and
    receiving a configuration confirmation during the configuration phase, the configuration confirmation indicative of associating the at least one associated covered light-emitting diode with the optical element.

10. The method of claim 1, wherein the optical element is a directional optical element and directs light output from the at least one associated covered light-emitting diode in a targeted direction.

11. The method of claim 1, wherein the optical element is an active optical element and utilizes the at least one associated covered light-emitting diode for backlighting.

12. The method of claim 11, wherein light output of the at least one of the associated covered light-emitting diode is harvested to power the optical element.

13. An active optical element, comprising:
    an active display panel;
    at least one controller coupled to said active display panel and providing content output to said active display panel;
    a power source electrically coupled to and powering said active display panel;
    wherein said active optical element is removably attachable over a surface of a plurality of light-emitting diodes; and
    one or more sensing light-emitting diodes of the plurality of light-emitting diodes configured to detect presence of said active optical element covering one or more portions of the active display panel;
    wherein said one or more sensing light-emitting diodes are configured to communicate said presence of the active optical element covering one or more portions of the active display panel to the at least one controller;
    wherein said active optical element has at least one identifiable property based on sensing of at least one physical characteristic of the optical element via at least one of the covered light-emitting diodes, said identifiable property utilized to adjust at least one lighting property of one or more covered light-emitting diodes of the light-emitting diodes when said active optical element is removably attached over the one or more covered light-emitting diodes.

14. The active optical element of claim 13, wherein said power source includes at least one light harvesting panel receiving light output from one or more of said covered light-emitting diodes when said active optical element is removably attached over the covered light-emitting diodes.

15. The active optical element of claim 14, wherein said light harvesting panel faces said covered light-emitting diodes when said active optical element is removably attached over the covered light-emitting diodes.

16. The active optical element of claim 13, further comprising a frame surrounding said active display panel and covering said power source.

17. The active optical element of claim 16, wherein said frame encloses said power source.

18. A lighting apparatus including a memory and a controller operable to execute instructions stored in the memory, comprising instructions to:
    identify presence of an optical element covering one or more portions of a surface of a plurality of light-emitting diodes, wherein said presence is based on sensing by one or more light-emitting diodes that are configured to sense the presence of the optical element covering one or more portions of the surface, said optical element being removably attachable over a surface of said plurality of light-emitting diodes;
    communicate the presence of the optical element covering one or more portions of the surface to the controller;
    associate the optical element with one or more of the covered LEDs the at least one covered light-emitting diode;
    identify at least one identifiable property of the optical element based on sensing of at least one physical characteristic of the optical element via at least one of the covered light-emitting diodes; and
    adjust at least one lighting property of the at least one associated covered light-emitting diode based on the identifiable property of the optical element.

19. A lighting system, comprising:
    at least one light source generating lighting having at least one adjustable lighting property;
    at least one sensing light-emitting diode configured to sense presence of an optical element covering one or more portions of a surface of a plurality of light-emitting diodes;
    at least one controller in electrical communication with said at least one light source and said at least one sensing light-emitting diode, wherein said at least one sensing light-emitting diode is configured to communicate the presence of the optical element covering one or more portions of the surface to said at least one controller;

wherein said at least one controller:

identifies presence of the optical element covering the at least one sensing light-emitting diode of a plurality of light-emitting diodes, said optical element being removably attachable over a surface of said plurality of light-emitting diodes;

associates the optical element with the at least one covered sensing light-emitting diode;

identifies at least one identifiable property of the optical element based on sensing of at least one physical characteristic of the optical element via at least one of the covered light-emitting diodes; and adjusts at least one lighting property of the at least one associated covered sensing light-emitting diode based on the identifiable property of the optical element.

\* \* \* \* \*